US012742121B2

(12) United States Patent
Mitsuda et al.

(10) Patent No.: US 12,742,121 B2
(45) Date of Patent: Sep. 22, 2026

(54) SULFONATE COMPOSITION

(71) Applicant: KAO CORPORATION, Tokyo (JP)

(72) Inventors: Yoshinori Mitsuda, Wakayama (JP); Keisuke Chiba, Wakayama (JP); Masato Nomura, Wakayama (JP); Yuuki Morishige, Wakayama (JP)

(73) Assignee: KAO CORPORATION, Tokyo (JP)

( * ) Notice: Subject to any disclaimer, the term of this patent is extended or adjusted under 35 U.S.C. 154(b) by 651 days.

(21) Appl. No.: 18/027,162

(22) PCT Filed: Dec. 21, 2021

(86) PCT No.: PCT/JP2021/047177

§ 371 (c)(1),
(2) Date: Mar. 20, 2023

(87) PCT Pub. No.: WO2022/138602

PCT Pub. Date: Jun. 30, 2022

(65) Prior Publication Data

US 2023/0332050 A1 Oct. 19, 2023

(30) Foreign Application Priority Data

Dec. 21, 2020 (JP) ................................. 2020-211481

(51) Int. Cl.

| | |
|---|---|
| ***C09K 23/10*** | (2022.01) |
| ***A01N 25/30*** | (2006.01) |
| ***A61K 8/46*** | (2006.01) |
| ***C11D 1/28*** | (2006.01) |

(52) U.S. Cl.

CPC .............. *C09K 23/10* (2022.01); *A01N 25/30* (2013.01); *A61K 8/466* (2013.01); *C11D 1/28* (2013.01)

(58) Field of Classification Search

None

See application file for complete search history.

(56) References Cited

U.S. PATENT DOCUMENTS

| | | | |
|---|---|---|---|
| 5,908,582 A | 6/1999 | Feustel et al. | |
| 6,194,473 B1 | 2/2001 | Lessard et al. | |
| 2007/0214999 A1* | 9/2007 | Meyer | C07C 309/17 106/14.05 |
| 2011/0240510 A1* | 10/2011 | De Poortere | C11D 3/392 206/524.7 |
| 2018/0201885 A1* | 7/2018 | Bittner | G03F 7/426 |

FOREIGN PATENT DOCUMENTS

| | | |
|---|---|---|
| CN | 109072129 A | 12/2018 |
| EP | 0130818 A2 | 1/1985 |
| GB | 1576019 A | 10/1980 |
| JP | S52-100423 A | 8/1977 |
| JP | S60-26098 A | 2/1985 |
| JP | S63-184000 A | 7/1988 |
| JP | H08-337567 A | 12/1996 |
| JP | H09-500884 A | 1/1997 |
| JP | 2002224552 A | 8/2002 |
| JP | 2012140571 A | 7/2012 |
| JP | 2018162446 A | 10/2018 |
| JP | 2018529989 A | 10/2018 |
| JP | 2019104852 A | 6/2019 |
| JP | 6674493 B2 | 4/2020 |
| WO | WO-2017204149 A1 | 11/2017 |
| WO | WO-2018034695 A1 | 2/2018 |
| WO | WO-2022138605 A1 | 6/2022 |

OTHER PUBLICATIONS

Combined Chinese Office Action and Search Report issued Dec. 26, 2024, in corresponding Chinese Patent Application No. 202180073809.5 (with partial English translation), 14 pages.

International Search Report issued Mar. 8, 2022 in PCT/JP2021/047177 (with English translation), 6 pages.

English translation of the International Preliminary Report on Patentability issued Jun. 29, 2023 in PCT/JP2021/047177, 6 pages.

Extended European Search Report issued Nov. 29, 2024, in corresponding European Patent Application No. 21910745.5, 8 pages.

* cited by examiner

*Primary Examiner* — Jeffrey D Washville

(74) *Attorney, Agent, or Firm* — Element IP, PLC

(57) ABSTRACT

In addition to an organic solvent (B), an inorganic metal compound (C), and water as component (D), a sulfonate composition disclosed in the present invention contains a compound (A) represented by ROOC—$(CH_2)_p$—CH$(SO_3M)$—$CH_2$—$(CH_2)_q$—COOR', where M represents a cation, R and R' independently represent a group selected from an alkyl group with 10 carbons and an alkenyl group with 10 carbons, p and q each represent a number of 0 to 18, and a total of p and q is 0 to 18. The mass ratios of components (A), (B), (C), and (D) to the total content of the components (A)-(D) are as follows: $0.05 \leq A/(A+B+C+D) \leq 0.71$, $B/(A+B+C+D) \geq 0.05$, $C/(A+B+C+D) > 0$, and $0.10 < D/(A+B+C+D) < 0.60$.

19 Claims, No Drawings

SULFONATE COMPOSITION

FIELD OF THE INVENTION

The present invention relates to a sulfonate composition.

BACKGROUND OF THE INVENTION

Sulfonates such as sulfonates or the like are anionic surfactants, and utilized alone or in combination with other components as detergent bases, emulsifiers, wetting agents, dispersants or the like in various fields.

US-A 2007/0214999 discloses a compound comprising a salt of a mono- and/or dialkyl ester of a sulfonated dicarboxylic acid, wherein the dicarboxylic acid contains 4 to 8 carbon atoms and the alkyl groups are derived from 2-propylheptanol, and a composition comprising this compound and a predetermined organic solvent.

JP-A 2002-224552 discloses an emulsifying and dispersing agent obtained by using a combination of two or more types of anionic surfactants (A) selected from the group consisting of the following: (A1) sulfate esters of predetermined adduct of an alphatic alcohol and an alkylene oxide, (A2) sulfonates of the adduct, (A3) ethers of a carboxylate and the adduct and (A4) phosphate esters of the adduct.

JP-A H9-500884 discloses a liquid composition comprising, water as a solvent or a cosolvent, a sulfosuccinic acid diester represented by a specific formula, wherein the cosolvent is a polymer which contains alkylene oxide units and is a liquid at 10° C.

SUMMARY OF THE INVENTION

Sulfonates are generally produced using aqueous reaction media, and obtained as reaction products including water. Taking distribution costs or the like into consideration, it is desirable that water and other components be reduced from the reaction products to increase the concentration of the main component sulfonates to a certain degree before using the reaction products to prepare secondary products.

It is considered that surfactants worth utilizing among sulfonates are diester-type compounds having an alkyl group or alkenyl group with a predetermined number of carbons because they have desirable foam behavior such as formation of fine foam when they are used in aqueous solutions and rapid foam disappearance, high cleaning power against solid fat stains, and others. However, turned out that compositions formulated with such sulfonates having an alkyl group or alkenyl group with a predetermined number of carbons and water may cause turbidity or precipitation and become non-uniform, resulting in an impaired appearance. Further, when such compositions return to liquid states after heated or frozen, their appearance is significantly deteriorated. This is most pronounced in the case where supersaturated inorganic salts are included in aqueous solutions of sulfonates. Particularly, if the aqueous solutions of sulfonates undergo changes in temperature, for example, operations such as storing them at high temperatures and thereafter bringing them back to room temperature, defrosting them after freezing at low temperatures or the like, the inorganic salts are deposited therein and these cause turbidity or precipitation.

The present invention provides a sulfonate composition containing a diester-type sulfonate having an alkyl group or alkenyl group with a predetermined number of carbons, the composition having a uniform appearance without turbidity or precipitation in a wide range of temperature regions even if containing inorganic salts, and having a uniform appearance even if heated or even if defrosted after frozen.

The present invention relates to a sulfonate composition containing:

(A) a compound represented by the following, formula (1) [hereinafter referred to as component (A)], $$\text{ROOC—(CH}_2)_p\text{—CH(SO}_3\text{M)—CH}_2\text{—(CH}_2)_q\text{—COOR'} \quad (1)$$

wherein M represents a cation, R and R' independently represent a group selected from alkyl groups with 10 carbons and alkenyl groups with 10 carbons, p and q each represent a number of 0 or more and 18 or less, and a total of p and q is 0 or more and 18 or less;

(B) an organic solvent [hereinafter referred to as component (B)];

(C) an inorganic metal compound [hereinafter referred to as component (C)]; and (D) water [hereinafter referred to as component (D)], wherein a mass ratio of the content of component (A) to a total content of components (A), (B), (C) and (D) [hereinafter referred to as A/(A+B+C+D)] is 0.05 or more and 0.71 or less, a mass ratio of the content of component (B) to the total content of components (A), (B), (C) and (D) [hereinafter referred to as B/(A+B+C+D)] is 0.05 or more, a mass ratio of the content of component (C) to the total content of components (A), (B), (C) and (D) [hereinafter referred to as C/(A+B+C+D)] is more than 0, and a mass ratio of the content of component (D) to the total content of components (A), (B), (C) and (D) [hereinafter referred to as D/(A+B+C+D)] is more than 0.10 and less than 0.60.

According to the present invention, provided is a sulfonate composition containing a diester-type sulfonate having an alkyl group or alkenyl group with a predetermined number of carbons, the composition having a uniform appearance without turbidity or precipitation even if containing inorganic salts, and having a uniform appearance even if defrosted after frozen. For example, the sulfonate composition of the present invention does not cause turbidlty or precipitation at general working temperatures or distribution temperatures (for example, 25° C. or more and 40° C. or less), and does not cause turbidity or precipitation even in a state where it is left standing outdoors or the like at high temperatures in summer or even if frozen in winter and undergoing recovery operations to liquid states by heating or the like. The degree of appearance of the sulfonate composition when it is defrosted after frozen ls hereinafter also referred co as freezing recoverability.

EMBODIMENTS OF THE INVENTION

In the present invention, a sulfonate composition excellent in uniformity (which means uniformity in a wide range of temperature regions, the same applies hereinafter) and freezing recoverability is obtained by making the mass ratios A/(A+B+C+D), B/(A+B+C+D), C/(A+B+C+D) and D/(A+B+C+D) each fall with in a predetermined range in the composition of a combination of components (A) to (D). This effect is obtained even in the composition containing component (A) at a high concentration. It is inferred that, in the present invention, deposition of components which affect uniformity or freezing recoverability, for example, inorganic metal compounds or the like is suppressed by the mass ratios each failing within a predetermined range. In general, component (A) is produced through the process of sulfonating a diester of an unsaturated dicarboxylic acid. A sulfonating agent used in this process or compounds derived therefrom may be deposited in the reaction product if remaining in a large amount. However, it is considered that the composition of the present invention makes it possible to obtain a composition which, even if including a sulfonating agent or compounds derived therefrom as inorganic metal compounds, suppresses the deposition of those compounds, and is excellent in uniformity and freezing recoverability. Therefore, for example, burdens involved in the removal of a sulfonating agent, neutralized products thereof or the like after production of component (A) can be reduced.

Component A is a compound represented by the following formula (1):

$$ROOC—(CH_2)_p—CH(SO_3M)—CH_2—(CH_2)_q—COOR' \quad (1)$$

wherein M represents a cation, R and R' independently represent a group selected from alkyl groups with 10 carbons and alkenyl groups with 10 carbons, p and q each represent a number of 0 or more and 18 or less, and a total of p and q is 0 or more and 18 less. Component (A) can be produced or obtained as, for example, a product obtained by sulfonating a diester maleic acid or fumaric acid and a salt thereof.

In the formula (1), M represents a cation, and specific examples include alkali metal ions such as a sodium ion, a potassium ion or the like and an ammonium ion.

In the formula (1), R and R' independently represent a group selected from al, groups with 10 carbons and alkenyl groups with 10 carbons R and R' independently represent preferably a group selected from branched-chain alkyl groups with 10 carbons and branched-chain alkenyl groups with 10 carbons, and more preferably a branched-chain alkyl group with 10 carbons from the viewpoints of uniformity in appearance and freezing recoverability. Examples of the alkyl groups with 10 carbons include n-decyl group, iso-decyl group, 2-propylheptyl group, 4-methyl 2-propylhexyl group and 5-methyl 2-propylhexyl group. Examples of the alkenyl groups with 10 carbons include n-decenyl group and iso-decenyl group from the viewpoints of uniformity in appearance and freezing recoverability. R and R' independently represent further preferably a group selected from 2-propylheptyl group, 4-methyl 2-propylhexyl group and 5-methyl 2-propylhexyl group from the viewpoints of uniformity in appearance and freezing recoverability.

In the formula (1), p and q each represent a number of 0 or more and 18 or less, and the total of p and q is 0 or more and 18 or less. The total of p and q is preferably 12 or less, more preferably 6 or less, further preferably 2 or less and furthermore preferably 1 or less from the viewpoint of availability. p and q may each represent 0. The compounds for which p and q each represent 0 are sulfosuccinic acid ester salts. Accordingly, component (A) may be a sulfosuccinic acid ester salt.

In the present invention, one or two or more types of component (A) can be used. From the viewpoints of uniform in appearance and freezing recoverability, the sulfonate composition of the present invention preferably contains as component (A), a compound for which one f or both R and R' represent 2-propylheptyl group.

The content of component (A) in the sulfonate composition of the present invention is preferably 30 mass % or more, more preferably 40 mass % or more, further preferably 50 mass % or more and furthermore preferably 60 mass % or more from the viewpoint of distribution costs, and preferably 70 mass % or less, more preferably 68 mass % or less and further preferably 66 mass % or less from the viewpoints of uniformity in appearance and freezing recoverability.

Component (B) is an organic solvent. Examples or component (B) include at least one selected from a monohydric alcohol and a polyhydric alcohol. Component (B) may be a monohydric alcohol or a polyhydric alcohol. Taking into consideration uses of the sulfonate composition of the present invention, for example, uses as a raw material for producing household products, component (B) is preferably one with less odor, and preferably a compound approved as a food additive, a cosmetic raw material or the like.

The monohydric alcohol may have 1 or more and 12 or less carbons. Examples of the monohydric alcohol include methanol, ethanol, 1-propanol, 1-butanol, 1-pentanol, 1-hexanol, 1-heptanol, 1-octanol, 1-nonanol, 2-nonanol, 5 nonanol, 1-decanol, 1-dodecanol, 3,5,5-trimethylhexan-1-ol, 2,6-dimethyl-4-heptanol, 2-propylheptanol, 4-methyl 2-propylhexanol, 5-methyl 2-propylhexanol or the like. The monohydric alcohol is preferably a compound selected from ethanol, 1-butanol and 1-propanol, and more preferably ethanol from the viewpoints of uniformity in appearance and freezing recoverability.

The polyhydric alcohol may have 2 or more and 12 or, less carbons. The polyhydric alcohol may be dihydric or more and hexahydric or less. Examples of the polyhydric alcohol include ethylene glycol, propylene glycol, 1,3-butanediol, 1,4-butanediol, 1,5-pentanediol, 1,6-hexanediol, 1,10-decanediol, diethylene glycol, triethylene glycol, tetraethylene glycol, dipropylene glycol, tripropylene glycol, glycerin, xylitol, sorbitol or the like. The polyhydric alcohol is preferably a compound selected from propylene glycol and glycerin, and more preferably propylene glycol from the viewpoints of uniformity in appearance and freezing recoverability.

Component (B) is preferably a compound selected from ethanol, 1-butanol, 1-propanol, glycerin and propylene glycol, and more preferably a compound selected from ethanol and propylene glycol from the viewpoints of uniformity in appearance and freezing recoverability.

The content of component (B) the sulfonate composition of the present invention is, from the viewpoints of uniformity in appearance and freezing recoverability, preferably 5 mass % or more, and from the viewpoint of versatility, preferably 90 mass % or less, and further from the viewpoint of the degree of purity of component (A), more preferably 50 mass % or less, further preferably 40 mass % or less, furthermore preferably 35 mas or less, furthermore preferably 25 mass % or less and furthermore preferably 20 mass % or less.

When component (B) is a monohydric alcohol, the content of component (B) in the sulfonate composition of the present invention is preferably 5 mass % or more, and preferably 30 mass % or less, more preferably 25 mass % or less and further preferably 20 mass % or less from the viewpoints of uniformity in appearance and freezing recoverability.

When component (B) is ethanol, the content of component (B) in the sulfonate composition of the present invention is preferably 5 mass % or more, and preferably 30 mass % or less, more preferably 25 mass % or less and further preferably 20 mass % or less from the viewpoints of uniformity in appearance and freezing recoverability.

When component (B) is a polyhydric alcohol, the content of component (B) in the sulfonate composition of the present invention is, from the viewpoints of uniformity in appearance and freezing recoverability, preferably 5 mass % or more and more preferably 10 mass % or more, and preferably 90 mass % or less, and further from the viewpoint of the degree of purity of component (A), more preferably 50 mass % or less, further preferably 40 mass % or less, furthermore preferably 35 mass % or less, furthermore preferably 25 mass % or less and furthermore preferably 20 mass %.

When component (B) is propylene glycol, the content of component (B) in the sulfonate composition of the present invention is, from the viewpoints of uniformity in appearance and freezing recoverability, preferably 5 mass % or more and more preferably 10 mass % or more, and from the viewpoint of versatility, preferably 90 mass % or less, and from the viewpoint of the degree of purity of component (A), more preferably 50 mass % or less, further preferably 40 mass % or less, furthermore preferably 35 mass % or less, furthermore preferably 25 mass % or less and furthermore preferably 20 mass % or less.

Component (C) is an inorganic metal compound. Examples of component (C) include at least one inorganic metal compound selected from metal sulfates, metal carbonates, metal hydrogen carbonates and metal hydroxides. More specific examples of component (C) include alkali metal sulfates such as sodium sulfate or the like, alkali metal carbonates such as sodium carbonate or the like, alkali metal hydrogen carbonates such as sodium hydrogen carbonate or the like, alkali metal hydroxides such as sodium hydroxide, potassium hydroxide or the like and alkaline earth metal hydroxides such as calcium hydroxide or the like. Component (C) may be an inorganic metal compound including no halogens.

Component (C) may be a compound formed by oxidization, neutralization or the like of a sulfonating agent used in a production process of component (A).

As the sulfonating agent used in a production process of component (A), for example, an inorganic sulfate selected from sulfites, hydrogen sulfites and disulfites is used. The sulfonating agent is preferably an inorganic sulfate selected from hydrogen sulfites and disulfites, and more preferably an inorganic sulfate selected from disulfites from the viewpoint of obtaining component (A) with small amounts of impurities. Examples of component (C) include the inorganic sulfates, hydrolyzed products of the inorganic sulfates, neutralized products of the inorganic sulfates, neutralized products of the hydrolyzed products of the inorganic sulfates, oxides of the inorganic sulfates, oxides of the hydrolyzed products of the inorganic sulfates and oxides of the neutralized products of the inorganic sulfates or the like.

Examples of component (C) include one or more selected from the following (C1) to (C4):

(C1) at least one compound selected from $MHSO_3$, $M_2SO_3$ and $M_2S_2O_5$ (wherein M represents a cation of a metal element);

(C2) a hydrolyzed product of compound (C1);

(C3) at least one neutralized product selected from a neutralized product of compound (C1) and a neutralized product of hydrolyzed product (C2); and (C4) at least one oxide selected from an oxide of compound (C1), an oxide of hydrolyzed product (C2) and an oxide of neutralized product (C3).

In component (C1), examples of 14 in the formulae include an alkali metal ion, an alkaline earth metal ion or the like, and an alkali metal ion is preferable from the viewpoint of versatility.

Examples of $MHSO_3$ of (C1) include potassium hydrogen sulfite, sodium hydrogen sulfite or the like.

Examples of $M_2SO_3$ of (C1) include potassium sulfite, sodium sulfite or the like.

Examples of $M_2S_2O_5$ of (C1) include potassium disulfite, sodium disulfite or the like.

Examples of hydrolyzed product (C2) include potassium hydrogen sulfite, sodium hydrogen sulfite or the like, for example, when compound (C1) is $M_2S_2O_5$.

Examples of neutralized product (C3) include a compound obtained by neutralizing a compound selected from compound (C1) and a hydrolyzed product thereof with a neutralizing agent. Examples of the neutralizing agent include, but are not particularly limited to, alkali metal carbonates such as sodium carbonate, potassium carbonate or the like, alkali metal hydrogen carbonates such as sodium hydrogen carbonate, potassium hydrogen carbonate or the like and alkyl metal hydroxides such as sodium hydroxide, potassium hydroxide or the like. The neutralizing agent is preferably selected from sodium carbonate, sodium hydrogen carbonate and sodium hydroxide from the viewpoints of uniformity in appearance and freezing recoverability. The neutralizing agent may be used in the form of powder or an aqueous solution.

Examples of oxide (C4) include a compound obtained by oxidizing a compound selected from compound (C1), hydrolyzed product (C2) and neutralized product (C3) with an oxidizing agent. Examples of the oxidizing agent include, but are not particularly limited to, alkali metal or alkaline earth metal peroxides, alkali metal or alkaline ear metal salts of hvpochlorous acid, potassium permanganate, hydrogen peroxide or the like. The oxidizing agent is preferably hydrogen peroxide from the viewpoints of uniformity appearance and freezing recoverability.

The sulfonate composition of the present invention may contain as component (C), (C1) at least one compound selected from $MHSO_3$, $M_2SO_3$ and $M_2SO_5$ (wherein M represents a cation).

The content of component (C) in the sulfonate composition of the present invention is more than 0 mass %, preferably 0.05 mass % or more and more preferably 0.1 mass % or more from the viewpoints of ease of production of the composition of the present invention, uniformity in appearance and freezing recoverability, and preferably 1.0 mass % or less and more preferably 0.9 mass % or less from the viewpoints of uniformity in appearance and freezing recoverability.

When component (B) is a monohydric alcohol, for example, ethanol, the content of component (B) is preferably adjusted in response to the content of component (C) in the composition from the viewpoints of uniformity in appearance and freezing recoverability. To be more specific, when component (B) is a monohydric alcohol, for example, ethanol, and the content of component (C) is less than 0.1 mass %, the content of component (B) in the sulfonate composition of the present invention is preferably 5 mass % or more and 30 mass % or less, and from the viewpoint of the degree of purity of component (A), more preferably 5 mass % or more and 25 mass % or less and further preferably 5 mass % or more and 20 mass % or less, and when component (B) is a monohydric alcohol, for example, ethanol, and the content of component (C) is 0.1 mass % or more, the content of component (B) is preferably 5 mass % or more and 20 mass % or less, more preferably 5 mass % or more and 15 mass % or less and further preferably 5 mass % or more and 10 mass % or less.

When component (B) is a polyhydric alcohol, for example, propylene glycol, the content of component (B) is preferably also adjusted in response to the content of component (C) from the viewpoints of uniformity in appearance and freezing recoverability. To be more specific, when component (B) is a polyhydric alcohol, for example, propylene glycol, and the content of component (C) is less than 0.1 mass %, the content of component (B) in the sulfonate composition of the present invention is preferably 10 mass % or more and 90 mass % or less, and from the viewpoint of the degree of purity of component (A), more preferably 10 mass % or more and 50 mass % or less, further preferably 10 mass % or more and 40 mass % or less, furthermore preferably 10 mass % or more and 35 mass % or less and furthermore preferably 10 mass % or more and 25 mass % or less, and when component (B) is a polyhydric alcohol, for example, propylene glycol, and the content of component (C) is 0.1 mass % or more, the content of component (B) is preferably 10 mass % or more and 33 mass % or less, and from the viewpoint of the degree of purity of component (A), more preferably 10 mass % or more and 30 mass % or less, further preferably 10 mass % or more and 25 mass % or less and furthermore preferably 10 mass % or more and 20 mass % or less.

Component (D) is water. Water that has been moderately purified and includes no impurities is preferably used. Well water or industrial water can also be used. Water with small amounts of impurities or hardness components is preferably used from the viewpoint of appearance of the sulfonate composition of the present invention. The water is preferably tap water or purified water, for example, ion exchange water from the viewpoints of uniformity in appearance and freezing recoverability The content of component (D) in the sulfonate composition of the present invention is preferably mass % or more, more preferably 5 mass % or more, further preferably 10 mass % or more, furthermore preferably 13 mass % or more, furthermore preferably 14 mass % or more, furthermore preferably 15 mass % or more, furthermore preferably 18 mass % or more and furthermore preferably 20 mass % or more, and preferably 50 mass % or less, more preferably 40 mass % or less and further preferably 30 mass % or less from the viewpoints of uniformity in appearance and freezing recoverability. The content of component (D) may be the balance of the composition excluding the total content of components (A), (B) and (C). Further, the content of component (D) may be the balance of the composition excluding the total content of components (A), (B) and (C) and optional components.

A/(A+B+C+D) in the sulfonate composition of the present invention is 0.05 or more and 0.71 or less. In one aspect, A/(A+B+C+D) in the sulfonate composition of the present invention may be 0.3 or more, further 0.4 or more and further 0.5 or more.

Further, B/(A+B+C+D) in the sulfonate composition of the present invention is 0.05 or more.

Further, C/(A+B+C+D) in the sulfonate composition of the present invention is more than 0. In another aspect, C/(A+B+C+D) in the sulfonate composition of the present invention may be less than 0.018 and further less than 0.016.

Further, D/(A+B+C+D) in the sulfonate composition of the present invention is more than 0.10 and less than 0.60. In another aspect, D/(A+B+C+D) in the sulfonate composition of the present invention may be 0.13 or more.

The mass ratio of the content of component (C) to the content f component (A) in the sulfonate composition of the present invention, C/A, may be 0.020 or less and further 0.017 or less from the viewpoint of deposition of inorganic metal compounds.

When component (B) is a monohydric alcohol, for example, ethanol the sulfonate composition of the present invention preferably satisfies the following condition (Ia) or (Ib) from the viewpoints of uniformity in appearance and freezing recoverability.

<Condition (Ia)>

Component (B) is a monohydric alcohol, and
A/(A+B+C+D) is 0.05 or more and 0.71 or less,
B/(A+B+C+D) is more than 0.05,
C/(A+B+C+D) is more than 0 and less than 0.001, and
D/(A+B+C+D) is more than 0.10 and 0.50 or less.

<Condition (Ib)>

Component (B) is a monohydric alcohol, and
A/(A+B+C+D) is 0.05 or more and 0.71 or less,
B/(A+B+C+D) is 0.05 or more,
C/(A+B+C+D) is 0.001 or more, and
D/(A+B+C+D) is 0.15 or more and less than 0.60.

A/(A+B+C+D) in condition (Ia) is 0.05 or more, preferably 0.3 or more, more preferably 0.4 or more and further preferably 0.5 or more, and 0.71 or less from the viewpoints of uniformity in appearance and freezing recoverability B/(A+B+C+D) condition (Ia) is, from the viewpoints of uniformity in appearance and freezing recoverability, preferably more than 0.05 and more preferably 0.10 or more, and from the viewpoint of improving the content of component (A), preferably 0.30 or less, more preferably 0.25 or less and further preferably 0.20 or less.

C/(A+B+C+D) in condition (Ia) is preferably more than 0 and less than 0.001 from the viewpoints of uniformity in appearance and freezing recoverability.

D/(A+5+C+D) in condition (Ia) is more than 0.10, and preferably 0.50 or less, more preferably 0.30 or less and further preferably 0.24 or less from the viewpoints of uniformity in appearance and freezing recoverability.

Condition (Ia) may further include the condition that the mass ratio of the total content of components (A) and (B) to the total content of components (A), (B) (C) and (D) [hereinafter referred to as (A+B)/(A+B+C+D)] is more than 0.10 and less than 0.90.

(A+B)/(A+B+C+D) is, from the viewpoints of uniformity in appearance and freezing recoverability, preferably more than 0.10, and from the viewpoint of improving the content of component (A), more preferably 0.50 or more and further preferably 0.71 or more, and preferably less than 0.90 and more preferably 0.86 of less.

Condition (Ia) includes an aspect in which one end and the other end of the numerical value range specified for each of A/(A+B+C+D), B/(A+B+C+D), C/(A+ B+C+D), D/(A+B+C+D) and (A+B)/(A+B+C+D) are arbitrarily combined.

A/(A+B+C+D) in condition (Ib) is 0.05 or more, preferably 0.3 or more, more preferably 0.4 or more and further preferably 0.5 or more, and 0.71 or less from the viewpoints of uniformity appearance and freezing recoverability.

B/(A+B+C+D) in condition (Ib) is 0.05 or more and preferably 0.15 or less from the viewpoints of uniformity in appearance, freezing recoverability and improvement of the content of component (A).

C/(A+B+C+D) in condition (Ib) is preferably 0.001 or more from the viewpoints of uniformity in appearance and freezing recoverability.

D/(A+B+C+D) in condition (Ib) is preferably 0.15 or more and more preferably 0.20 or more from the viewpoints of uniformity in appearance and freezing recoverability, and less than 0.60, preferably less than 0.35 and more preferably 0.30 or less from the viewpoints uniformity in appearance, freezing recoverability and improvement of the content of component (A).

Condition (Ib) may further include the condition that (A+B)/(A+B+C+D) is 0.10 or more and 0.80 or less.

Condition (Ib) includes an aspect in which one end and the other end of the numerical value range specified for each of A/(A+B+C+D), B/(A+B+C+D), C/(A+B+C+D), D/(A+B+C+D) and (A+B)/(A+B+C+D) ate arbitrarily combined.

Further, when component (B) is a polyhydric alcohol, for example, a polyhydric alcohol such as propylene glycol or the like, the sulfonate composition of the present invention preferably satisfies the following condition (IIa) or (IIb) from the viewpoints of uniformity in appearance and freezing recoverability.

<Condition (IIa)>

Component (B) is a polyhydric alcohol, and
A/(A+B+C+D) is 0.05 or more and 0.71 of less,
B/(A+B+C+D) is more than 0.05 and 0.90 less,
C/(A+B+C+D) is more than 0 and less than 0.001, and
D/(A+B+C+D) is more than 0.10 and less than 0.50.

<Condition (II-b)>

Component (B) is a polyhydric alcohol, and
A/(A+B+C+D) is 0.05 or more and 0.71 less,
B/(A+B+C+D) is more than 0.05 and less than 0.40,
C/(A+B+C+D) is 0.001 or more, and
D/(A+B+C+D) is 0.13 or more and less than 0.50.

A/(A+B+C+D) in condition (IIa) is 0.05 or more, preferably 0.3 or more, more preferably 0.4 or more and further preferably 0.5 or more, and 0.71 or less from the viewpoints of uniformity in appearance and freezing recoverability.

B/(A+B+C+D) in condition (IIa) is, from the viewpoints of uniformity in appearance and freezing recoverability, preferably more than 0.05 and more preferably 0.10 or more, and preferably 0.90 or less, and from the viewpoint of improving the content of component (A), more preferably 0.50 or less, further preferably 0.35 or less and furthermore preferably 0.20 or less.

C/(A+B+C+D) in condition (IIa) is preferably more than 0 and less than 0.001 from the viewpoints of uniformity in appearance and freezing recoverability.

D/(A+B+C+D) in condition (IIa) is, from the viewpoints of uniformity in appearance and freezing recoverability, more than 0.10 and preferably 0.14 or more, and preferably less than 0.50, and from the viewpoint of improving the content of component (A), more preferably less than 0.40, further preferably less than 0.30 and further preferably 0.25 or less.

Condition (IIa) may further include the condition that (A+B)/(A+B+C+D) is 0.40 or more and 0.95 or less.

(A+B)/(A+B+C+D) in condition (IIa) is, from the viewpoints of uniformity in appearance and freezing recoverability, preferably 0.40 or more and more preferably 0.50 or more, and preferably 0.95 or less, and from the viewpoint of improving the content of component (A), more preferably 0.90 or less.

Condition (IIa) may further include the condition that the mass ratio of the content of component (D) to the total content of components (A) and (D) [hereinafter referred to as D/(A+D)] is 0.17 or more and 0.90 or less, 0.17 or more and 0.65 or less, 0.17 or more and 0.55 or less, 0.17 or more and 0.45 or less, or 0.17 or more and less than 0.30. D/(A+D) is preferably 0.27 or less.

Condition (IIa) includes an aspect in which one end and the other end of the numerical value range specified for each of A/(A+B+C+D) B/(A+B+C+D), C/(A+B+C+D) D/(A+B+C+D), (A+B)/(A+B+C+D) and D/(A+D) are arbitrarily combined.

A/(A+B+C+D) in condition (IIb) is 0.05 or more, preferably 0.3 or more, further preferably 0.4 or more and furthermore preferably 0.5 or more, and 0.71 or less from the viewpoints of uniformity in appearance and freezing recoverability.

B/(A+B+C+D) in condition (IIb) is preferably more than 0.05 and more preferably 0.10 or more, and preferably less than 0.40, more preferably 0.25 or less and further preferably less than 0.16 from the viewpoints of uniformity in appearance and freezing recoverability.

C/(A+B+C+D) in condition (IIb) is preferably 0.001 or more.

D/(A+B+C+D) in condition (IIb) is preferably 0.13 or more, more preferably more than 0.15 and further preferably 0.18 or more from the viewpoints of uniformity in appearance and freezing recoverability, and preferably less than 0.50, more preferably less than 0.40, further preferably less than 0.30 and furthermore preferably 0.25 or less from the viewpoints of uniformity in appearance, freezing recoverability and improvement of the content of component (A).

Condition (IIb) may further include the condition that (A+B)/(A+B+C+D) is 0.40 or more and 0.95 or less.

(A+B)/(A+B+C+D) in condition (IIb) may be preferably 0.40 or more and more preferably 0.50 or more, and preferably 0.95 or less and 0.90 or less from the viewpoints of uniformity in appearance and freezing recoverability.

Condition (IIb) may further include the condition that the mass ratio of the content of component (D) to the total content components (A) and (D) [hereinafter referred to as D/(A+D)] is 0.15 or more and 0.50 or less, 0.15 or more and 0.45 or less, 0.15 or more and 0.40 or less, 0.15 or more and 0.30 or less, or 0.15 or more and 0.25 or less. D/(A+D) is preferably 0.30 or less.

Condition (IIb) includes an aspect in which one end and the other end of the numerical value range specified for each of A/(A+B+C+D), B/(A+B+C+D), C/(A+B+C+D), D/(A+B+C+D), (A+B)/(A+B+C+D) and D/(A+D) are arbitrarily combined.

Further, conditions (Ia) to (IIb) can be combined with the contents mentioned earlier, or with the other mass ratios, contents or the like described later.

The total content of components (A), (B), (C) and (D) in the sulfonate composition of the present invent is preferably 90 mass % or more, more preferably 95 mass % or more and further preferably 97 mass % or more, and preferably 100 mass % or less from the viewpoint of distribution costs.

The sulfonate composition of the present invention may contain (Y) a compound represented by the following formula (2) [hereinafter referred to as component (Y)]:

$$ROOC—(CH_2)_n—CH{=}CH—(CH_2)_m—COOR' \quad (2)$$

wherein R and R' independently represent a group selected from alkyl groups with 10 carbons and alkenyl groups with 10 carbons, m and n each represent a number of 0 or more and 18 or less, and a total of m and n is 0 or more and 18 or less. Component (Y) can be produced or obtained as, for example, diesters of maleic acid or fumaric acid.

In the formula (2), R and R' independently represent a group selected from alkyl groups with 10 carbons and alkenyl groups with 10 carbons. R and R' independently represent preferably a group selected from branched-chain alkyl groups with 10 carbons and branched-chain alkenyl groups with 10 carbons, and more preferably a branched-chain alkyl group with 10 carbons. Examples of the alkyl groups with 10 carbons include n-decyl group, iso-decyl group, 2-propylheptyl group, 4-methyl 2-propylhexyl group and 5-methyl 2-propylhexyl group. Examples of he alkenyl groups with 10 carbons include n-decenyl group and iso-decenyl group. R and R' independently represent further preferably a group selected from 2-propylheptyl group, 4-methyl 2-propylhexyl group and 5-methyl 2-propylhexyl group.

In the formula (2), m and n each represent a number of 0 or more and 18 or less, and the total of m and n is 0 or more and 18 or less. m and n may each represent 0. The compounds for which m and n each represent 0 are diesters of maleic acid or fumaric acid. Component may be, for example, diesters of maleic acid.

In the present invention, one or two or more types of component (Y) can be used. From the viewpoints of uniformity in appearance and freezing recoverability, the sulfonate composition of the present invention preferably contains as component (Y), a compound for which one of or both R and R' represent 2-propylheptyl group.

When the sulfonate composition of the present invention contains component (Y), the content of component (Y) in the composition is preferably 4 mass % or less, more preferably 3 mass % or less and further preferably 2.5 mass % or less, and more than 0 mass % from the viewpoints of uniformity in appearance, freezing recoverability and distribution costs.

The mass ratio of the content of component (Y) to the content of component (A) in the sulfonate composition of the present invention is, from the viewpoints of uniformity in appearance, freezing recoverability and distribution costs, preferably 0.065 or less, more preferably 0.050 or less, further preferably 0.045 or less, further-more preferably 0.040 or less and further-more preferably 0.035 or less, and from the viewpoint of availability, the lower limit is preferably more than 0, more preferably 0.0010 or more and further preferably 0.010 or more. This mass ratio is the mass ratio of the content of component (Y) to the content of component W, and may also be referred to as Y/A.

The mass ratio of the content of component (Y) to the total content of components (A), (B), (C) and (D) in the sultanate composition of the present invention from the viewpoints of uniformity in appearance, freezing recoverability and distribution costs, preferably 0.045 or less, more preferably 0.040 or less, further preferably 0.035 or less, furthermore preferably 0.030 or less and furthermore preferably 0.020 or less, and from the viewpoint of availability, preferably more than 0, more preferably 0.0007 or more and further preferably 0.0070 or more. This mass ratio is the mass ratio of the content of component (Y) to the total content of components (A), (B), (C) and (D), and may also be referred to as Y/(A+B+C+D).

The mass ratio of the total content of components (A) and (Y) to the total content of components (A), (B) (C) and (D) in the sulfonate composition of the present invention is, from the viewpoints of uniformity in appearance and freezing recoverability, preferably 0.05 or more, and from the viewpoint of improving the content of component (A), preferably more than 0.60, and from tie viewpoints of uniformity in appearance and freezing recoverability, preferably less than 0.75 and more preferably 0.73 or less. This mass ratio is the mass ratio of the total content of components (A) and (Y) to the tot- l content of components (A), (B), (C) and (D), and may also be referred to as (A+Y)/(A+B+C+D).

The total content of components (A) and (Y) in the sulfonate composition of the present invention is, for example, 30 mass % or more, further 40 mass % or more, further 50 mass % or more and further 60 mass % or more from the viewpoint of distribution costs, and may be, for example, 74 mass % or less, further 73 mass % or less, further 72.5 mass % or less, further 72 mass % or less, further 71 mass % or less, further 70.5 mass % or less, further 70 mass % or less, further 69 mass % or less, further 68.5 mass % or less, further 68 mass % or less and further 66 mass % or less from the viewpoints of uniformity in appearance and freezing recoverability.

Further, when the sulfonate composition of the present invention contains component (Y), and component (B) is a monohydric alcohol, for example, ethanol, the total content of components (A) and (Y) in the composition is preferably 30 mass % or more and less than 75 mass %, and the content of component (Y) preferably 4.0 mass % or less from the viewpoints of uniformity in appearance and freezing recoverability. The content of component (D) is preferably selected from the range mentioned earlier. In this case as well, the content of component (D) in the composition may be the balance of the composition excluding the total content of components (A), (B), (C) and (Y). Further, the content of component. (D) may be the balance of the composition. excluding the total content of components (A), (B), (C) and (Y) and other optional components.

Further, when the sulfonate composition of the present invention contains component (Y), and component (B) is a polyhydric alcohol, for example, propylene glycol, the total content of components (A) and (Y) it the composition is preferably 30 mass % or more and less than 75 mass %, and the content of component (Y) is preferably 4 mass % or less from the viewpoints of uniformity in appearance and freezing recoverability. The content of component (D) is preferably selected from the range mentioned earlier. In this case as well, the content of component (D) in the composition may be the balance of the composition excluding the total content of components (A), (B), (C) and (Y). Further, the content of component (D) may be the balance of the composition excluding the total content of components (A), (B), (C) and (Y) and other optional components.

The sulfonate composition of the present invention can contain optional components other than component (Y). For example, the composition can contain monoesters of maleic acid or fumaric acid, 2-propylheptanol, 4-methyl 2-propylhexanol, 5-methyl propylhexanol, sulfosuccinic acid monoester salts, maleic acid or fumaric acid salts and others, as well as additives or adjusters such as pH buffers, antiseptics or the like.

The proportion of components (A), (B) and (C) in components other than component (D) in the sulfonate composition of the present invention is preferably 95 mass % or more, and preferably 100 mass % or less, and may 100 mass % from the viewpoint of uniformity in appearance.

Further, when the sulfonate composition of the present invention contains component (Y), the proportion of components (A), (B), (C) and (Y) in components other than component (D) is preferably 95 mass % or more, and preferably 100 mass % or less, and may be 100 mass % from the viewpoint of uniformity in appearance.

The sulfonate composition of the present invention can be used as a raw material for products such as, for example, detergents, solubilizers, treatment agents, modifiers, wetting agents, penetrating agents, agrochemicals, paints, cosmetics and emulsifiers or the like.

The present invention provides a method for producing a sulfonate composition (hereinafter also referred to as the producing method of the present invention) including, sulfonating a diester compound represented by the following formula (1a) with an inorganic sulfate under the presence of components (B) and (D) to produce a mixture containing components (A), (B), (C) and (D), $$ROOC—(CH_2)_p—CH{=}CH—(CH_2)_q—COOR' \quad (1a)$$

wherein R and R' independently represent a group selected from alkyl groups with 10 carbons and alkenyl groups with 10 carbons, p and q each represent a number of 0 or more and 18 or less, and a total of p and q is 0 or more and 18 or less, wherein the composition of the mixture is adjusted such that a mass ratio of the content of component (A) to a total content of components (A), (B), (C) and D [hereinafter referred to as A/(A+B+C+D)] is 0.05 or more and 0.71 or less, a mass ratio of the content of component (B) to the total content of components (A), (B), (C) and (D) [hereinafter referred to as B/(A+B+C+D)] is 0.05 or more, a mass ratio of the content of component (C) to the total content of components (A), (B), (C) and (D) [hereinafter referred to as C/(A+B+C+D) ] is more than 0, and a mass ratio of the content of component (D) to the total content of components (A), (B), (C) and (D) [hereinafter referred to as D/(A+B+C+D)] is more than 0.10 and less than 0.60.

The matters stated in the sulfonate composition of the present invention can be appropriated applied to the producing method of the present invention. The preferable examples of components (A) to (D), the applications of conditions (I) to (II) or the like in the producing method of the present invention may also be the same as those in the sulfonate composition of the present invention. The sulfonate composition of the present invention may be produced by the producing method of the present invention.

The following aspects of the present invention are described by way of example. The matters specified in the aspects can be mutually applied in an appropriate manner.

<1>

A sulfonate composition containing:

(A) a compound represented by the following formula (1) [hereinafter referred to as component (A)], $$\mathrm{ROOC—(CH_2)_p—CH(SO_3M)—CH_2—(CH_2)_q—COOR'} \quad (1)$$

wherein M represents a cation, R and R' independently represent a group selected from alkyl groups with 10 carbons and alkenyl groups with 10 carbons, p and q each represent a number of 0 or more and 18 or less, and a total of p and q 0 or more and 18 or less;

(B) an organic solvent [hereinafter referred to as component (B)];

(C) an inorganic metal compound [hereinafter referred to as component (C)]; and (D) water [hereinafter referred to as component (D)], wherein a mass ratio of the content of component (A) to a total content of components (A), B), (C) and (D) [hereinafter referred to as A/(A+B+C+D)] is 0.05 or more and 0.71 or less, a mass ratio of the content of component (B) to the total content of components (A), (B), (C) and [hereinafter referred to as B/(A+B+C+D)] is 0.05 more, a mass ratio of the content of component (C) to the total content of components (A), (B), (C) and (D) [hereinafter referred to as C/(A+B+C+D)] is more than 0, and a mass ratio of the content of component (D) to the total content of components (A), (B), (C) and (C) [hereinafter referred to as D/(A+B+C+D)] is more than 0.10 and less than 0.60.

<2>

The sulfonate composition according to <1>, wherein M in the formula represents a cation selected from a sodium ion, a potassium ion and an ammonium ion.

<3>

The sulfonate composition according to <1> or <2>, wherein R and R' in the formula (I) independently represent a branched-chain alkyl group with 10 carbons and a branched-chain alkenyl group with 10 carbons, and further a branched-chain alkyl group with 10 carbons.

<4>

The sulfonate composition according to any of <1> to <3>, wherein R and R' in the formula (1) independently represent a group selected from n-decyl group, iso-decyl group, 2-propylheptyl group, 4-methyl 2-propylhexyl group, 5-methyl 2-propylhexyl group, n-decenyl group and iso-decenyl group, and further a group selected from 2-propylheptyl group, 4-methyl 2-propylhexyl group and 5-methyl 2-propylhexyl group.

<5>

The sulfonate composition according to any of <1> to <4>, wherein the total of p and g in the formula (1) is 0 or more, and 18 or less, preferably 12 or less, more preferably 6 or less, further preferably 2 less and furthermore preferably 1 or less, or 0.

<6>

The sulfonate composition according to any of <1> to <5>, wherein p and q in the formula (1) each represent 0.

<7>

The sulfonate composition according to any of <1> to <6>, containing as component (A), a compound of the formula (1) in which one of or both R and R' represent 2-propylheptyl group.

<8>

The sulfonate composition according to any of <1> to <7>, wherein the content of (A) component in the sulfonate composition is preferably 30 mass % or more, more preferably40 mass % or more, further preferably 50 mass % or more and furthermore preferably 60 mass % or more, and preferably 70 mass % or less, more preferably 68 mass % or less and further preferably 66 mass % or less.

<9>

The sulfonate composition according to any of <1> to <8>, wherein component (B) is at least one selected from a monohydric alcohol and a polyhydric alcohol, and further a monohydric alcohol or a polyhydric alcohol.

<10>

The sulfonate composition according to <9>, wherein the monohydric alcohol is a monohydric alcohol with 1 or more and 12 or less carbons, further a monohydric alcohol selected from methanol, ethanol, 1-propanol, 1-butanol, 1-pentanol, 1-hexanol, 1-heptanol, 1-octanol, 1-nonanol, 2-nonanol, 5-nonanol, 1-decanol, 1-dodecanol, 3,5,5-trimethylhexan-1-ol, 2,6-dimethyl-4-heptanol, 2-propylheptanol, 4-methyl 2-propylhexanol and 5-methyl 2-propylhexanol, further a monohydric alcohol selected from ethanol, 1-butanol and 1-propanol, and further ethanol.

<11>

The sulfonate composition according to <9> or <10>, wherein the polyhydric alcohol is a polyhydric alcohol with 2 or more and 12 or less carbons.

<12>

The sulfonate composition according to any of <9> to <11>, wherein the polyhydric alcohol is a dihydric or more and hexahydric or less polyhydric alcohol.

<13>

The sulfonate composition according to any of <9> to <12>, wherein the polyhydric alcohol is a polyhydric alcohol selected from ethylene glycol, propylene glycol, 1,3-butanediol, 1,4-butanediol, 1,5-pentanediol, 1,6-hexanediol, 1,10-decanediol, diethylene glycol, triethylene glycol, tetraethylene glycol, dipropylene glycol, tripropylene glycol, glycerin, xylitol and sorbitol, further a polyhydric alcohol selected from propylene glycol and glycerin, and further propylene glycol.

<14>

The sulfonate composition according to any of <1> to <13>, wherein component (B) is a compound selected from ethanol, 1-butanol, 1-propanol, glycerin and propylene glycol, and further a compound selected from ethanol and propylene glycol.

<15>

The sulfonate composition according to any of <1> to <14>, wherein the content of component (B) in the sulfonate composition is preferably 5 mass % or more, and preferably 90 mass % or less, more preferably 50 mass % or less, further preferably 40 mass % or less, furthermore preferably 35 mass % or less, furthermore preferably 25 mass % or less and furthermore preferably 20 mass % or less.

<16>

The sulfonate composition according to any of <1> to <15>, wherein component (B) is a monohydric alcohol, and further ethanol, and the content of component (B) in the sulfonate composition is preferably 5 mass % or more, and preferably 30 mass % or less, more preferably 25 mass % or less and further preferably 20 mass % or less.

<17>

The sulfonate composition according to any of <1> to <15>, wherein component (B) is a polyhydric alcohol, and further propylene glycol, and the content of component (B) in the sulfonate composition is preferably 5 mass or more and more preferably 10 mass % or more, and preferably 90 mass % or less, more preferably 50 mass % or less, further preferably 40 mass % or less, furthermore preferably 35 mass % or less, furthermore preferably 25 mass % or less and furthermore preferably 20 mass %.

<18>

The sulfonate composition according to any of <1> to <17>, wherein component (C) is at least one inorganic metal compound selected from metal sulfates, metal carbonates, metal hydrogen carbonates and metal hydroxides, further at least one selected from alkali metal sulfates, alkali metal carbonates, alkali metal hydrogen carbonates, alkali metal hydroxides and alkaline earth metal hydroxides, further at least one selected from sodium sulfate, sodium carbonate, sodium hydrogen carbonate, sodium hydroxide, potassium hydroxide and calcium hydroxide, and further sodium sulfate.

<19>

The sulfonate composition according to any of <1> to <18>, wherein component (C) is an inorganic metal compound including no halogens.

<20>

The sulfonate composition according to any of <1> to <19>, wherein component (C) is one or more selected from the following (C1) to (C4):

(C1) at least one compound selected from $MHSO_3$, $M_2SO_3$ and $M_2S_2O_5$ (wherein M represents a cation of a metal element);

(C2) a hydrolyzed product of compound (C1);

(C3) at least one neutralized product selected from a neutralized product of compound (C1) and a neutralized product of hydrolyzed product (C2); and (C4) at least one oxide selected from an oxide of compound (C1), an oxide of hydrolyzed product (C2) and an oxide of neutralize product (C3).

<21>

The sulfonate composition according to any <1> to <20>, wherein the content of component (C) in the sulfonate composition is more than 0 mass %, preferably 0.05 mass % or more and more preferably 0.1 mass % or more, and preferably 1.0 mass % or less and more preferably 0.9 mass % or less.

<22>

The sulfonate composition according to any of <1> to <21>, wherein component (B) is a monohydric alcohol, and further ethanol, the content of component (C) in the composition is less than 0.1 mass %, and the content of component (B) is preferably 5 mass % or more and 30 mass % or less, and from the viewpoint of the degree of purity of component (A), more preferably 5 mass % or more and 25 mass % or less and further preferably 5 mass % or more and 20 mass % or less.

<23>

The sulfonate composition according to any of <1> to <21>, wherein component (B) is a monohydric alcohol, and further ethanol, the content of component (C) in the composition is 0.1 mass % or more, and the content of component (B) is preferably 5 mass % or more and 20 mass % or less, more preferably 5 mass % or more and 15 mass % or less and further preferably 5 mass % or more and 10 mass %

<24>

The sulfonate composition according to any of <1> to <21>, wherein component (B) is a polyhydric alcohol, and further propylene glycol, the content of component (C) is less than 0.1 mass %, and the content of component (B) is preferably 10 mass % or more and 90 mass % or less, more preferably 10 mass % or more and 50 mass % or less, further preferably 10 mass % or more and 40 mass % or less, furthermore preferably 10 mass % or more and 35 mass % or less and furthermore preferably 10 mass % or more and 25 mass % or less.

<25>

The sulfonate composition according to any of <1> to <21>, wherein component (B) is a polyhydric alcohol, and further propylene glycol, the content of component (C) is 0.1 mass % or more, and the content of component (B) is preferably 10 mass % or more and 33 mass % or less, more preferably 10 mass % or more and 30 mass % or less, further preferably 10 mass % or more and 25 mass % or less and furthermore preferably 10 mass % or more and 20 mass % or less.

<26>

The sulfonate composition according to any of <1> to <25>, wherein the content of component (D) in the sulfonate composition is preferably 4 mass % or more, more preferably 5 mass % or more, further preferably 10 mass % or more, furthermore preferably 13 mass % or more, furthermore preferably 14 mass % or more, furthermore preferably 15 mass % or more, furthermore preferably 18 mass % or more and furthermore preferably 20 mass % or more, and preferably 50 mass % or less, more preferably 40 mass % or less and further preferably 30 mass % or less.

<27>

The sulfonate composition according to any <1> to <26>, wherein a mass ratio of the content of component (C) to the content of component (A), C/A, is 0.020 or less and further 0.017 or less.

<28>

The sulfonate composition according to any of <1> to <27>, wherein component (B) is a monohydric alcohol, and the composition satisfies the following condition (Ia) or (Ib):

<Condition (Ia)> component (B) is a monohydric alcohol, and

A/(A+B+C+D) is 0.05 or more and 0.71 or less,

B/(A+B+C+D) is more than 0.05,

C/(A+B+C+D) is more than 0 and less than 0.001, and

D/(A+B+C+D) is more than 0.10 and 0.50 or less;

<Condition (Ib)> component (B) is a monohydric alcohol, and

A/(A++C+D) is 0.05 or more and 0.71 less,

B/(A++C+D) is 0.05 or more,

C/(A+B+C+D) is 0.001 or more, and

D/(A+B+C+D) is 0.15 or more and less than 0.60.

<29>

The sulfonate composition according to <28>, wherein B/(A+B+C+D) is condition (Ia) is preferably more than 0.05 and more preferably 0.10 or more, and preferably 0.30 or less, more preferably 0.25 or less and further preferably 0.20 or less.

<30>

The sulfonate composition according to <28> or <29>, wherein C/(A+B+C+D) in condition less than 0.001.

<31>

The sulfonate composition according, to any of <28> to <30>, wherein D/(A+B+C+D) in condition (Ia) is preferably more than 0.10, and preferably 0.50 or less, more preferably 0.30 or less and further preferably 0.24 or less.

<32>

The sulfonate composition according, to any of <28> to <31>, wherein in condition (Ia), A/(A+B+C+D) is 0.05 or more, preferably 0.3 or more, further preferably 0.4 or more and furthermore preferably 0.5 or more, and 0.71 or less, B/(A+B+C+D) is preferably more than 0.05 and more preferably 0.10 or more, and preferably 0.30 or less, more preferably 0.25 or less and further preferably 0.20 or less, C/(A+B+C+D) is more than 0 and less than 0.001, and D/(A+B+C+D) is more than 0.10, and preferably 0.50 or less, more preferably 0.30 or less and further preferably 0.24 or less.

<33>

The sulfonate composition according to any of <28> to <32>, wherein condition (Ia) further includes a condition that a mass ratio of a total content of components (A) and (B) to the total content of components (A), (B), (C) and (D) is preferably more than 0.10, more preferably 0.50 or more and further preferably 0.71 or more, and less than 0.90 and more preferably 0.86 or less.

<34>

The sulfonate composition according, to any of <28> to <33>, wherein B/(A+B+C+D) in condition (Ib) is preferably 0.15 or more.

<35>

The sulfonate composition according to any of <28> to <34>, wherein C/(A+B+C+D) in condition (Ib) is preferably 0.001 or more.

<36>

The sulfonate composition according to any of <28> to <35>, wherein D/(A+B+C+D) in condition (Ib) is preferably 0.15 or more and more preferably 0.20 or more, and less than 0.60, preferably less than 0.35 and more preferably 0.30 or less.

<37>

The sulfonate composition according to any of <28> to <36>, wherein in condition (Ib), A/(A+B+C+D) is 0.05 or more, preferably 0.3 or more, more preferably 0.4 or more and furthermore preferably 0.5 or more, and 0.71 or less, B/(A+B+C+D) is 0.05 or more, and preferably 0.15 or less, C/(A+B+C+D) is preferably 0.001 or more, and D/(A+B+C+D) is preferably 0.15 or more and more preferably 0.20 or more, and less than 0.60, preferably less than 0.35 and more preferably 0.30 less.

<38>

The sulfonate composition according to any <28> to <37>, wherein condition (Ib) further includes a condition that a mass ratio of a total content of components (A) and (B) to the total content of components (A), (B), (C) and (D) is 0.10 or more and 0.80 or less.

<39>

The sulfonate composition according to any of <1> to <27>, wherein component (B) is a polyhydric alcohol, the composition satisfies the following (IIa) or (IIb):

<Condition (IIa)> component (B) is a polyhydric alcohol, and

A/(A+B+C+D) is 0.05 or more and 0.71 or less,

B/(A+B+C+D) is more than 0.05 and 0.90 or less,

C/(A+B+C+D) is more than 0 and less than 0.001, and

D/(A+B+C+D) is more than 0.10 and less than 0.50;

>Condition (IIb)> component (B) is a polyhydric alcohol, and

A/(A+B+C+D) is 0.05 or more and 0.71 less,

B/(A+B+C+D) is more than 0.05 and less than 0.40,

C/(A+B+C+D) is 0.001 or more, and

D/(A+B+C+D) is 0.13 or more and less than 0.50.

<40>

The sulfonate composition according to <39>, wherein B/(A+B+C+D) in condition (IIa) is preferably more than 0.05 and more preferably 0.10 or more, and preferably 0.90 or less, more preferably 0.50 or less, further preferably 0.35 or less and furthermore preferably 0.20 or less.

<41>

The sulfonate composition according to <39> or <40>, wherein C/(A+B+C+D) in condition (IIa) is less than 0.001.

<42>

The sulfonate composition according to any of <39> to <41>, wherein D/(A+B+C+D) in condition (IIa) is preferably 0.14 or more, and preferably less than 0.50, more preferably less than 0.40, further preferably less than 0.30 and further preferably 0.25 or less.

<43>

The sulfonate composition according to any <39> to <42>, wherein in condition (IIa), A/(A+B+C+D) is 0.05 or more, preferably 0.3 or more, more preferably 0.4 or more and further preferably 0.5 or more, and 0.71 or less, B/(A+B+C+D) is preferably more than 0.05 and more preferably 0.10 or more, and preferably 0.90 or less, more preferably 0.50 or less, further preferably 0.35 or less and furthermore preferably 0.20 or less, C/(A+B+C+D) is preferably more than 0 and less than 0.001, and D/(A+B+C+D) is more than 0.10 and preferably 0.14 or more, and preferably less than 0.50, more preferably less than 0.40, further preferably less than 0.30 and further preferably 0.25 or less.

<44>

The sulfonate composition according to any of <39> to <43>, wherein condition (IIa) further includes a condition that a mass ratio of a total content of components (A) and (B) to the total content of components (A), (B), (C) and (D) is 0.40 or more and preferably 0.50 or more, and 0.95 or less and preferably 0.90 or less.

<45>

The sulfonate composition according, to any of <39> to <44>, wherein condition (IIa) further includes a condition that a mass ratio of the content of component (D) to a total content of components (A) and (D) is 0.17 or more and 0.90 or less, 0.17 or more and 0.65 or less, 0.17 or more and 0.55 of less, 0.17 or more and 0.45 or less, 0.17 or more and less than 0.30, or 0.17 or more and 0.27 or less.

<46>

The sulfonate composition according to any of <39> to <45>, wherein B/(A+B+C+D) in condition (IIb) is preferably more than 0.05 and more preferably 0.10 or more, and preferably less than 0.40, more preferably 0.25 or less and further preferably less than 0.16.

<47>

The sulfonate composition according to any of <39> to <46>, wherein C/(A+B+C+D) in condition (IIb) is preferably 0.001 or more.

<48>

The sulfonate composition according to any of <39> to <47>, wherein D/(A+B+C+D) in condition (IIb) is preferably 0.13 or more, more preferably more than 0.15 and further preferably 0.18 or more, and preferably less than 0.50, more preferably less than 0.40, further preferably less than 0.30 and furthermore preferably 0.25 or less.

<49>

The sultanate composition according to any <39> to <48>, wherein is condition (IIb), A/(A+B+C+D) is 0.05 or more, preferably 0.3 or more, more preferably 0.4 or more and further preferably 0.5 or more, and 0.71 or less, B/(A+B+C+D) is preferably more than 0.05 and more preferably 0.10 or more, and preferably less than 0.40, more preferably 0.25 or less and further preferably less than 0.16, C/(A+B+C+D) is preferably 0.001 or more, and D/(A+B+C+D) is preferably 0.13 or more, more preferably more than 0.15 and further preferably 0.18 or more, and preferably less than 0.50, more preferably less than 0.40, further preferably less than 0.30 and furthermore preferably 0.25 or less.

<50>

The sulfonate composition according to any <39> to <49>, wherein condition (IIb) further includes a condition that a mass ratio of a total content of components (A) and (B) to the total content of components (A), (B), (C) and (D) is 0.40 or more and preferably 0.50 or more, and 0.95 or less and preferably 0.90 or less.

<51>

The sultanate composition according to any <39> to <50>, wherein condition (IIb) further includes a condition that a mass ratio of the content component (D) to a total content of components (A) and (D) is 0.15 or more and 0.50 or less, 0.15 or more and 0.45 or less, 0.15 or more and 0.40 or less, 0.15 or more and 0.30 or less, or 0.15 or more and 0.25 or less.

<52>

The sulfonate composition according to any <1> to <51>, wherein A/(A+B+C+D) is 0.3 or more.

<53>

The sulfonate composition according to any of <1> to <52>, wherein A/(A+B+C+D) is 0.4 or more.

<54>

The sulfonate composition according to any <1> to <53>, wherein A/(A+B+C+D) is 0.5or more.

<55>

The sulfonate composition according to any of <1> to <54>, wherein C/(A+B+C+D) is less than 0.018.

<56>

The sulfonate composition according to any of <1> to <55>, wherein C/(A+B+C+D) is less than 0.016.

<57>

The sulfonate composition according to any <1> to <56>, wherein D/(A+B+C+D) is 0.13 or more.

<58>

The sulfonate composition according to any of <1> to <57>, wherein the total content of components (A), (B), (C) and (D) in the sulfonate composition is preferably 90 mass % or more, more preferably 95 mass % or more and further preferably 97 mass % or more, and preferably 100 mass % or less.

<59>

The sulfonate composition according to any of <1> to <58>, wherein a proportion of components (A), (B) and (C) in components other than component (D) is preferably 95 mass % or more, and preferably 100 mass % or less, or 100 mass %.

<60>

The sulfonate composition according to any of <1> to <59>, containing (Y) a compound represented by the following formula (2) [hereinafter referred to as component (Y)]:

$$ROOC—(CH_2)_n—CH═CH—(CH_2)_m—COOR' \quad (2)$$

wherein R and R' independently represent a group selected from alkyl groups with 10 carbons and alkenyl groups with 10 carbons, m and n each represent a number of 0 or more and 18 or less, and a total of m and n is 0 or more and 18 or less.

<61>

The sulfonate composition according to <60>, wherein R and R' in the formula (2) independently represent a group selected from branched-chain alkyl groups with 10 carbons and branched-chain alkenyl groups with 10 carbons, and further a branched-chain alkyl group with 10 carbons.

<62>

The sulfonate composition according to <60> or <61>, wherein R and R' in the formula (2) independently represent a group selected from n-decyl group, iso-decyl group, 2-propylheptyl group, 4-methyl 2-propylhexyl group, 5-methyl 2-propylhexyl group, n-decenyl group and iso-decenyl group, and further a group selected from 2-propylheptyl group, 4-methyl 2-propylhexyl group and 5-methyl 2-propylhexyl group.

<63>

The sulfonate composition according to any of <60> to <62>, wherein m and n in the formula (2) each represent 0.

<64>

The sulfonate composition according to any <60> to <63>, containing as component (Y), a compound of the formula (2) in which one of or both R and R' represent 2-propylheptyl group.

<65>

The sulfonate composition according to any of <60> to <64>, wherein the content of component (Y) in the sulfonate composition is preferably 4 mass % or less, more preferably 3 mass % or less and further preferably 2.5 mass % or less, and more than 0 mass %.

<66>

The sulfonate composition according to any of <60> to <65>, wherein a mass ratio of the content of component (Y) to the content of component (A), Y/A, is preferably 0.065 or less, more preferably 0.050 or less, further preferably 0.045 or less, furthermore preferably 0.040 or less and furthermore preferably0.035 or less, and preferably more than 0, more preferably 0.0010 or more and further preferably 0.010 or more.

<67>

The sulfonate composition according to any of <60> to <66>, wherein a mass ratio of the content of component (Y) the total content of components (A), (B), (C) and (D), Y/(A+B+C+D), is preferably 0.045 or less, more preferably 0.040 or less, further preferably 0.035 or less, furthermore preferably 0.030 or less and furthermore preferably 0.020 or less, and preferably more than 0, more preferably 0.0007 or more and further preferably 0.0070 or more.

<68>

The sulfonate composition according to any of <60> to <67>, wherein a mass ratio of a total content of components (A) and (Y) to the total content of components (A), (B), (C) and (D), (A+Y)/(A+B+C+D), is preferably 0.05 or more and preferably more than 0.60, and preferably less than 0.75 and more preferably 0.73 or less.

<69>

The sulfonate composition according to any of <60> to <68>, wherein a total content of components (A) and (Y) in the sultanate composition is 30 mass % or more, further 40 mass % or more, further 50 mass % or more and further 60 mass % or more, and 74 mass % or less, further 73 mass % or less, further 72.5 mass % or less, further 72 mass % or less, further 71 mass % or less, further 70.5 mass % or less, further 70 mass % or less, further 69 mass % or less, further 68.5 mass % or less, further 68 mass % or less and further 66 mass % or less.

<70>

The sulfonate composition according to any of <60> to <69>, wherein the composition contains component (Y), component (B) is a monohydric alcohol and further ethanol, a total content of components (A) and (Y) in the composition is preferably 30 mass % or more and less than 75 mass %, and the content of component (Y) is preferably 4.0 mass % or less.

<71>

The sulfonate composition according to any of <60> to <69>, wherein the composition contains component (Y), component (B) is a polyhydric alcohol and further propylene glycol, a total content of components (A) and (Y) in the composition is preferably 30 mass % or more and less than 75 mass %, and the content of component (Y) is preferably 4 mass % or less.

<72>

The sulfonate composition according to any of <60> to <71>, wherein the composition contains component (Y), and a proportion of components (A), (B), (C) and (Y) in components other than component (D) is preferably 95 mass % or more, and preferably 100 mass % or less, or 100 mass %.

EXAMPLES

The content of each component in the react products of the production examples described later and the compositions in Examples was determined by each of the following methods:

(I) Sodium Sulfosuccinate Ester Content (Mass %)

it was determined in accordance with the test method for synthetic detergents in JIS K 3362;

(II) Maleic Acid Diester Content (Mass %)

a maleic acid diester was quantified by gas chromatography;

(III) Ethanol Content (Mass %)

ethanol was quantified by gas chromatography;

(IV) Propylene Glycol Content (Mass %)

propylene glycol was quantified by gas chromatography;

(V) Water Content (mass %)

it was determined in accordance with Test methods for water content of chemical products in JIS K 0068;

(VI) Sodium Sulfate Content (Mass %)

sodium sulfate was quantified using "automatic potentiometric titrator" manufactured by Kyoto Electronics Manufacturing Co., Ltd.; and (VII) Sodium Sulfite Content (Mass %)

sodium sulfite was quantified using "ICS-2100" manufactured by Thermo Fisher Scientific.

Production Example 1

A maleic acid diester was obtained in conformance with Example 2 of US-A 2007/0214999.

Next, the maleic acid diester (100 parts by mass), sodium disulfite (26.4 parts by mass), ion exchange water (17.3 carts by mass) and ethanol (35.5 parts by mass) were put in a 1-L glass reaction vessel, and reacted at 115° C. in a publicly-known manner. The mixture was cooled to 60° C. or less, and after the residual sodium hydrogen sulfite was oxidized with 30% hydrogen peroxide water, the pH was adjusted to 5 with a 10% aqueous sodium hydroxide solution. Subsequently, the solvents a sodium sulfate were removed by filtration, distillation under reduced pressure, freeze drying or the like to obtain a reaction product including a sodium sulfosuccinate ester. In this reaction product, the sodium sulfosuccinate ester content: 96.4 mass %, a maleic acid diester: 1.5 mass %, the loss on drying: 1.2 mass % and the sodium sulfate content: 0.07 mass %. The sodium sulfosuccinate ester included in this reaction product was a compound of the formula (1) in which M represents a sodium ion, p and q each represent 0, and R and R' each represent 2-propylheptyl group [hereinafter referred to as sodium sulfosuccinate ester (1)]. Further, the maleic acid diester included in this reaction product was a compound of the formula (2) which m and n each represent 0, and R and R' each represent 2-propylheptyl group.

Production Example 2

A maleic acid diester was obtained in conformance with Example 2 of US-A 2007/0214999.

Next, sodium sulfosuccinate ester (2) was obtained in conformance with Production Example 2 of JP-A 2002-224552, provided that alkylene oxide adduct (E-1) in that Production Example 2 was not used, and the diesterized product was replaced with the above maleic acid diester. The reaction time for sulfonation was then adjusted to obtain reaction products with different amounts of residual sodium sulfate and sodium sulfite. The sodium sulfosuccinate ester included in each of these reaction products was a compound of the formula (1) in which M represents a sodium ion, p and q each represent 0, and R and R' each represent 2-propylheptyl group [hereinafter referred to as sodium sulfosuccinate ester (2)].

Examples 1 to 5 and Comparative Examples 1 to 2

(1) Sulfonate Composition

The sulfonate compositions having any of the compositions in Tables 1 to 5 were each prepared by mixing the reaction product obtained in production example 1 or 2 and water. The components listed below were then added as necessary to adjust the content. Further, the reaction product produced in production example 1 was used in the form of a composition obtained by drying it when formulating the sulfonate compositions. Further, the reaction product produced in production example 2 was used as-is when formulating the sulfonate compositions.

Ethanol: manufactured by FUJIFILM Wako Pure Chemical Corporation, a special grade reagent Propylene glycol: manufactured by FUJIFILM Wako Pure Chemical Corporation, a special grade reagent Sodium sulfate: manufactured by FUJIFILM Wako Pure Chemical Corporation, a special grade reagent (2) Evaluation (2-1) Evaluation of Uniformity 30 g of each sulfonate composition prepared was put in a tightly-sealable glass vessel (with a capacity of 50 cc), and after the vessel was sealed tightly, the sample was left to stand for 24 hours in a thermostatic bats whose temperature was kept constant under each temperature condition (25° C., 35° C., 40° C. or 60° C.), and the appearance and fluidity of the sample were thereafter observed. The results are shown in the tables.

(2-2) Evaluation of Freezing Recoverability 30 g of each sulfonate composition prepared was in a tightly-sealable glass vessel (with a capacity of 50 cc), and with the vessel sealed tightly, the sample was stored (completely solidified) in a freezer at 0° C. or less for 24 hours. Subsequently, after confirmed to have turned to a liquid state in a thermostatic bath whose temperature was kept constant at 40° C., the sample was left to stand for 2 hours, and the appearance of the sample was thereafter observed. The results are shown in the tables.

TABLE 1

| | | | Example 1 | | | | |
|---|---|---|---|---|---|---|---|
| | | | 1-1 | 1-2 | 1-3 | 1-4 | 1-5 |
| Sulfosuccinate ester composition | Composition (mass %) | (A) Sodium sulfosuccinate ester (1)*1 | 65 | 60 | 70 | 70 | 60 |
| | | (B) Ethanol | 10 | 20 | 10 | 15 | 10 |
| | | (C) Sodium sulfate | 0.05 | 0.05 | 0.05 | 0.05 | 0.04 |
| | | (D) Ion exchange water | 23.95 | 19.05 | 18.85 | 13.85 | 29.0 |
| | | (Y) Maleic acid diester*1 | 1.0 | 0.9 | 1.1 | 1.1 | 0.9 |
| | | Total amount | 100 | 100 | 100 | 100 | 100 |
| | A/(A + B + C + D) (mass ratio) | | 0.66 | 0.61 | 0.71 | 0.71 | 0.61 |
| | B/(A + B + C + D) (mass ratio) | | 0.10 | 0.20 | 0.10 | 0.15 | 0.10 |
| | C/(A + B + C + D) (mass ratio) | | 0.0005 | 0.0005 | 0.0005 | 0.0005 | 0.0004 |
| | D/(A + B + C + D) (mass ratio) | | 0.24 | 0.19 | 0.19 | 0.14 | 0.29 |
| | (A + B)/(A + B + C + D) (mass ratio) | | 0.76 | 0.81 | 0.81 | 0.86 | 0.71 |
| | Uniformity | 25° C. | Clear liquid state, no precipitation | Clear liquid state, no precipitation | Clear liquid state, no precipitation | Clear liquid state, no precipitation | Clear liquid state, no precipitation |
| | | 35° C. | Clear liquid state, no precipitation | Clear liquid state, no precipitation | Clear liquid state, no precipitation | Clear liquid state, no precipitation | Clear liquid state, no precipitation |
| | | 40° C. | Clear liquid state, no precipitation | Clear liquid state, no precipitation | Clear liquid state, no precipitation | Clear liquid state, no precipitation | Clear liquid state, no precipitation |
| | | 60° C. | Clear liquid state, no precipitation | Clear liquid state, no precipitation | Clear liquid state, no precipitation | Clear liquid state, no precipitation | Clear liquid state, no precipitation |
| | Freezing recoverability | | Clear liquid state, no precipitation | Clear liquid state, no precipitation | Clear liquid state, no precipitation | Clear liquid state, no precipitation | Clear liquid state, no precipitation |

| | | | Example 1 | | | | |
|---|---|---|---|---|---|---|---|
| | | | 1-6 | 1-7 | 1-8 | 1-9 | 1-10 |
| Sulfosuccinate ester composition | Composition (mass %) | (A) Sodium sulfosuccinate ester (1)*1 | 50 | 50 | 40 | 40 | 30 |
| | | (B) Ethanol | 10 | 30 | 10 | 30 | 20 |
| | | (C) Sodium sulfate | 0.04 | 0.04 | 0.03 | 0.03 | 0.02 |
| | | (D) Ion exchange water | 39.2 | 19.2 | 49.3 | 29.3 | 49.5 |
| | | (Y) Maleic acid diester*1 | 0.8 | 0.8 | 0.6 | 0.6 | 0.5 |
| | | Total amount | 100 | 100 | 100 | 100 | 100 |

TABLE 1-continued

| | | | | | | |
|---|---|---|---|---|---|---|
| A/(A + B + C + D) (mass ratio) | | 0.50 | 0.50 | 0.40 | 0.40 | 0.30 |
| B/(A + B + C + D) (mass ratio) | | 0.10 | 0.30 | 0.10 | 0.30 | 0.20 |
| C/(A + B + C + D) (mass ratio) | | 0.0004 | 0.0004 | 0.0003 | 0.0003 | 0.0002 |
| D/(A + B + C + D) (mass ratio) | | 0.39 | 0.19 | 0.50 | 0.30 | 0.50 |
| (A + B)/(A + B + C + D) (mass ratio) | | 0.60 | 0.81 | 0.50 | 0.70 | 0.50 |
| Uniformity | 25° C. | Clear liquid state, no precipitation | Clear liquid state, no precipitation | Clear liquid state, no precipitation | Clear liquid state, no precipitation | Clear liquid state, no precipitation |
| | 35° C. | Clear liquid state, no precipitation | Clear liquid state, no precipitation | Clear liquid state, no precipitation | Clear liquid state, no precipitation | Clear liquid state, no precipitation |
| | 40° C. | Clear liquid state, no precipitation | Clear liquid state, no precipitation | Clear liquid state, no precipitation | Clear liquid state, no precipitation | Clear liquid state, no precipitation |
| | 60° C. | Clear liquid state, no precipitation | Clear liquid state, no precipitation | Clear liquid state, no precipitation | Clear liquid state, no precipitation | Clear liquid state, no precipitation |
| Freezing recoverability | | Clear liquid state, no precipitation | Clear liquid state, no precipitation | Clear liquid state, no precipitation | Clear liquid state, no precipitation | Clear liquid state, no precipitation |

*[1]The reaction product of production example 1 was used.

TABLE 2

| | | | | Example 2 | | | |
|---|---|---|---|---|---|---|---|
| | | | | 2-1 | 2-2 | 2-3 | 2-4 |
| Sulfosuccinate ester composition | Composition (mass %) | (A) | Sodium sulfosuccinate ester (1)*[1] | 70 | 68 | 65 | 60 |
| | | (B) | Ethanol | 9 | 10 | 5 | 10 |
| | | (C) | Sodium sulfate | 0.3 | 0.3 | 1.0 | 1.0 |
| | | (D) | Ion exchange water | 19.6 | 20.6 | 28.0 | 28.1 |
| | | (Y) | Maleic acid diester*[1] | 1.1 | 1.1 | 1.0 | 0.9 |
| | | | Total amount | 100 | 100 | 100 | 100 |
| A/(A + B + C + D) (mass ratio) | | | | 0.71 | 0.69 | 0.66 | 0.61 |
| B/(A + B + C + D) (mass ratio) | | | | 0.09 | 0.10 | 0.05 | 0.10 |
| C/(A + B + C + D) (mass ratio) | | | | 0.0030 | 0.0030 | 0.0101 | 0.0101 |
| D/(A + B + C + D) (mass ratio) | | | | 0.20 | 0.21 | 0.28 | 0.28 |
| (A + B)/(A + B + C + D) (mass ratio) | | | | 0.799 | 0.789 | 0.707 | 0.706 |
| Uniformity | 25° C. | | | Clear liquid state, no precipitation | Clear liquid state, no precipitation | Clear liquid state, no precipitation | Clear liquid state, no precipitation |
| | 35° C. | | | Clear liquid state, no precipitation | Clear liquid state, no precipitation | Clear liquid state, no precipitation | Clear liquid state, no precipitation |
| | 40° C. | | | Clear liquid state, no precipitation | Clear liquid state, no precipitation | Clear liquid state, no precipitation | Clear liquid state, no precipitation |
| | 60° C. | | | Clear liquid state, no precipitation | Clear liquid state, no precipitation | Clear liquid state, no precipitation | Clear liquid state, no precipitation |
| Freezing recoverability | | | | Clear liquid state, no precipitation | Clear liquid state, no precipitation | Clear liquid state, no precipitation | Clear liquid state, no precipitation |

| | | | | Example 2 | Comparative example 1 | |
|---|---|---|---|---|---|---|
| | | | | 2-5 | 1-1 | 1-2 |
| Sulfosuccinate ester composition | Composition (mass %) | (A) | Sodium sulfosuccinate ester (1)*[1] | 65 | 75 | 76 |
| | | (B) | Ethanol | 10 | 20 | 4 |
| | | (C) | Sodium sulfate | 1.0 | 0.3 | 0.3 |
| | | (D) | Ion exchange water | 23.0 | 3.5 | 18.5 |
| | | (Y) | Maleic acid diester*[1] | 1.0 | 1.2 | 1.2 |
| | | | Total amount | 100 | 100 | 100 |

TABLE 2-continued

| | | | |
|---|---|---|---|
| A/(A + B + C + D) (mass ratio) | 0.66 | 0.76 | 0.77 |
| B/(A + B + C + D) (mass ratio) | 0.10 | 0.20 | 0.04 |
| C/(A + B + C + D) (mass ratio) | 0.0101 | 0.0030 | 0.0030 |
| D/(A + B + C + D) (mass ratio) | 0.23 | 0.04 | 0.19 |
| (A + B)/(A + B + C + D) (mass ratio) | 0.758 | 0.962 | 0.810 |
| Uniformity 25° C. | Clear liquid state, no precipitation | Turbidity, precipitation | Turbidity, precipitation |
| 35° C. | Clear liquid state, no precipitation | Turbidity, precipitation | Turbidity, precipitation |
| 40° C. | Clear liquid state, no precipitation | Turbidity, precipitation | Turbidity, precipitation |
| 60° C. | Clear liquid state, no precipitation | Turbidity, precipitation | Turbidity, precipitation |
| Freezing recoverability | Clear liquid state, no precipitation | Turbidity, precipitation | Turbidity, precipitation |

*[1]The reaction product of production example 1 was used.

TABLE 3

| | | | Example 3 | | | | |
|---|---|---|---|---|---|---|---|
| | | | 3-1 | 3-2 | 3-3 | 3-4 | 3-5 |
| Sulfosuccinate ester composition | Composition (mass %) | (A) Sodium sulfosuccinate ester (1)*[1] | 65 | 60 | 70 | 70 | 50 |
| | | (B) Propylene glycol | 10 | 20 | 10 | 15 | 33 |
| | | (C) Sodium sulfate | 0.05 | 0.05 | 0.05 | 0.05 | 0.04 |
| | | (D) Ion exchange water | 23.95 | 19.05 | 18.85 | 13.85 | 16.19 |
| | | (Y) Maleic acid diester*[1] | 1 | 0.9 | 1.1 | 1.1 | 0.8 |
| | | Total amount | 100 | 100 | 100 | 100 | 100 |
| | A/(A + B + C + D) (mass ratio) | | 0.66 | 0.61 | 0.71 | 0.71 | 0.50 |
| | B/(A + B + C + D) (mass ratio) | | 0.10 | 0.20 | 0.10 | 0.15 | 0.33 |
| | C/(A + B + C + D) (mass ratio) | | 0.0005 | 0.0005 | 0.0005 | 0.0005 | 0.0004 |
| | D/(A + B + C + D) (mass ratio) | | 0.24 | 0.19 | 0.19 | 0.14 | 0.16 |
| | D/(A + D) (mass ratio) | | 0.27 | 0.24 | 0.21 | 0.17 | 0.24 |
| | (A + B)/(A + B + C + D) (mass ratio) | | 0.76 | 0.81 | 0.81 | 0.86 | 0.84 |
| | Uniformity | 25° C. | Clear liquid state, no precipitation | Clear liquid state, no precipitation | Clear liquid state, no precipitation | Clear liquid state, no precipitation | Clear liquid state, no precipitation |
| | | 35° C. | Clear liquid state, no precipitation | Clear liquid state, no precipitation | Clear liquid state, no precipitation | Clear liquid state, no precipitation | Clear liquid state, no precipitation |
| | | 40° C. | Clear liquid state, no precipitation | Clear liquid state, no precipitation | Clear liquid state, no precipitation | Clear liquid state, no precipitation | Clear liquid state, no precipitation |
| | | 60° C. | Clear liquid state, no precipitation | Clear liquid state, no precipitation | Clear liquid state, no precipitation | Clear liquid state, no precipitation | Clear liquid state, no precipitation |
| | Freezing recoverability | | Clear liquid state, no precipitation | Clear liquid state, no precipitation | Clear liquid state, no precipitation | Clear liquid state, no precipitation | Clear liquid state, no precipitation |

| | | | Example 3 | | | |
|---|---|---|---|---|---|---|
| | | | 3-6 | 3-7 | 3-8 | 3-9 |
| Sulfosuccinate ester composition | Composition (mass %) | (A) Sodium sulfosuccinate ester (1)*[1] | 50 | 40 | 40 | 30 |
| | | (B) Propylene glycol | 10 | 40 | 15 | 50 |
| | | (C) Sodium sulfate | 0.04 | 0.03 | 0.03 | 0.02 |
| | | (D) Ion exchange water | 39.19 | 19.35 | 44.35 | 19.52 |
| | | (Y) Maleic acid diester*[1] | 0.8 | 0.6 | 0.6 | 0.5 |
| | | Total amount | 100 | 100 | 100 | 100 |

TABLE 3-continued

| | | | | | | | |
|---|---|---|---|---|---|---|---|
| A/(A + B + C + D) (mass ratio) | | | | 0.50 | 0.40 | 0.40 | 0.30 |
| B/(A + B + C + D) (mass ratio) | | | | 0.10 | 0.40 | 0.15 | 0.50 |
| C/(A + B + C + D) (mass ratio) | | | | 0.0004 | 0.0003 | 0.0003 | 0.0002 |
| D/(A + B + C + D) (mass ratio) | | | | 0.39 | 0.19 | 0.45 | 0.20 |
| D/(A + D) (mass ratio) | | | | 0.44 | 0.33 | 0.53 | 0.39 |
| (A + B)/(A + B + C + D) (mass ratio) | | | | 0.60 | 0.80 | 0.55 | 0.80 |
| Uniformity | 25° C. | | | Clear liquid state, no precipitation | Clear liquid state, no precipitation | Clear liquid state, no precipitation | Clear liquid state, no precipitation |
| | 35° C. | | | Clear liquid state, no precipitation | Clear liquid state, no precipitation | Clear liquid state, no precipitation | Clear liquid state, no precipitation |
| | 40° C. | | | Clear liquid state, no precipitation | Clear liquid state, no precipitation | Clear liquid state, no precipitation | Clear liquid state, no precipitation |
| | 60° C. | | | Clear liquid state, no precipitation | Clear liquid state, no precipitation | Clear liquid state, no precipitation | Clear liquid state, no precipitation |
| Freezing recoverability | | | | Clear liquid state, no precipitation | Clear liquid state, no precipitation | Clear liquid state, no precipitation | Clear liquid state, no precipitation |

| | | | | Example 3 | | | |
|---|---|---|---|---|---|---|---|
| | | | | 3-10 | 3-11 | 3-12 | 3-13 |
| Sulfosuccinate ester composition | Composition (mass %) | (A) | Sodium sulfosuccinate ester (1)*[1] | 30 | 5 | 5 | 5 |
| | | (B) | Propylene glycol | 20 | 75 | 90 | 50 |
| | | (C) | Sodium sulfate | 0.02 | 0.004 | 0.004 | 0.004 |
| | | (D) | Ion exchange water | 49.52 | 19.92 | 4.92 | 44.92 |
| | | (Y) | Maleic acid diester*[1] | 0.5 | 0.1 | 0.1 | 0.1 |
| | | | Total amount | 100 | 100 | 100 | 100 |
| A/(A + B + C + D) (mass ratio) | | | | 0.30 | 0.05 | 0.05 | 0.05 |
| B/(A + B + C + D) (mass ratio) | | | | 0.20 | 0.75 | 0.90 | 0.50 |
| C/(A + B + C + D) (mass ratio) | | | | 0.0002 | 0.00004 | 0.00004 | 0.00004 |
| D/(A + B + C + D) (mass ratio) | | | | 0.50 | 0.20 | 0.05 | 0.45 |
| D/(A + D) (mass ratio) | | | | 0.62 | 0.80 | 0.50 | 0.90 |
| (A + B)/(A + B + C + D) (mass ratio) | | | | 0.50 | 0.80 | 0.95 | 0.55 |
| Uniformity | 25° C. | | | Clear liquid state, no precipitation | Clear liquid state, no precipitation | Clear liquid state, no precipitation | Clear liquid state, no precipitation |
| | 35° C. | | | Clear liquid state, no precipitation | Clear liquid state, no precipitation | Clear liquid state, no precipitation | Clear liquid state, no precipitation |
| | 40° C. | | | Clear liquid state, no precipitation | Clear liquid state, no precipitation | Clear liquid state, no precipitation | Clear liquid state, no precipitation |
| | 60° C. | | | Clear liquid state, no precipitation | Clear liquid state, no precipitation | Clear liquid state, no precipitation | Clear liquid state, no precipitation |
| Freezing recoverability | | | | Clear liquid state, no precipitation | Clear liquid state, no precipitation | Clear liquid state, no precipitation | Clear liquid state, no precipitation |

*[1]The reaction product of production example 1 was used.

TABLE 4

| | | | | Example 4 | | | | |
|---|---|---|---|---|---|---|---|---|
| | | | | 4-1 | 4-2 | 4-3 | 4-4 | 4-5 |
| Sulfosuccinate ester composition | Composition (mass %) | (A) | Sodium sulfosuccinate ester (1)*[1] | 70 | 65 | 65 | 60 | 70 |
| | | (B) | Propylene glycol | 10 | 10 | 15 | 15 | 15 |
| | | (C) | Sodium sulfate | 0.3 | 1 | 1 | 1 | 0.30 |
| | | (D) | Ion exchange water | 18.6 | 23 | 18 | 23.1 | 13.2 |
| | | (Y) | Maleic acid diester*[1] | 1.1 | 1 | 1 | 0.9 | 1.5 |
| | | | Total amount | 100 | 100 | 100 | 100 | 100 |

TABLE 4-continued

| | | | | | |
|---|---|---|---|---|---|
| A/(A + B + C + D) (mass ratio) | 0.71 | 0.66 | 0.66 | 0.61 | 0.71 |
| B/(A + B + C + D) (mass ratio) | 0.10 | 0.10 | 0.15 | 0.15 | 0.15 |
| C/(A + B + C + D) (mass ratio) | 0.0030 | 0.0101 | 0.0101 | 0.0101 | 0.0030 |
| D/(A + B + C + D) (mass ratio) | 0.19 | 0.23 | 0.18 | 0.23 | 0.13 |
| D/(A + D) (mass ratio) | 0.21 | 0.26 | 0.22 | 0.28 | 0.16 |
| (A + B)/(A + B + C + D) (mass ratio) | 0.81 | 0.76 | 0.81 | 0.76 | 0.86 |
| Uniformity 25° C. | Clear liquid state, no precipitation | Clear liquid state, no precipitation | Clear liquid state, no precipitation | Clear liquid state, no precipitation | Clear liquid state, no precipitation |
| Uniformity 35° C. | Clear liquid state, no precipitation | Clear liquid state, no precipitation | Clear liquid state, no precipitation | Clear liquid state, no precipitation | Clear liquid state, no precipitation |
| Uniformity 40° C. | Clear liquid state, no precipitation | Clear liquid state, no precipitation | Clear liquid state, no precipitation | Clear liquid state, no precipitation | Clear liquid state, no precipitation |
| Uniformity 60° C. | Clear liquid state, no precipitation | Clear liquid state, no precipitation | Clear liquid state, no precipitation | Clear liquid state, no precipitation | Clear liquid state, no precipitation |
| Freezing recoverability | Clear liquid state, no precipitation. | Clear liquid state, no precipitation | Clear liquid state, no precipitation | Clear liquid state, no precipitation | Clear liquid state, no precipitation |

| | | | | Example 4 | | | |
|---|---|---|---|---|---|---|---|
| | | | | 4-6 | 4-7 | 4-8 | 4-9 |
| Sulfosuccinate ester composition | Composition (mass %) | (A) | Sodium sulfosuccinate ester (1)*[1] | 60 | 50 | 60 | 50 |
| | | (B) | Propylene glycol | 12.9 | 10.7 | 20 | 25 |
| | | (C) | Sodium sulfate | 0.25 | 0.21 | 0.25 | 0.21 |
| | | (D) | Ion exchange water | 25.6 | 38.0 | 18.5 | 23.7 |
| | | (Y) | Maleic acid diester*[1] | 1.3 | 1.1 | 1.3 | 1.1 |
| | | | Total amount | 100 | 100 | 100 | 100 |
| A/(A + B + C + D) (mass ratio) | | | | 0.61 | 0.51 | 0.61 | 0.51 |
| B/(A + B + C + D) (mass ratio) | | | | 0.13 | 0.11 | 0.20 | 0.25 |
| C/(A + B + C + D) (mass ratio) | | | | 0.0026 | 0.0021 | 0.0026 | 0.0021 |
| D/(A + B + C + D) (mass ratio) | | | | 0.26 | 0.38 | 0.19 | 0.24 |
| D/(A + D) (mass ratio) | | | | 0.30 | 0.43 | 0.24 | 0.32 |
| (A + B)/(A + B + C + D) (mass ratio) | | | | 0.74 | 0.61 | 0.81 | 0.76 |
| Uniformity | 25° C. | | | Clear liquid state, no precipitation | Clear liquid state, no precipitation | Clear liquid state, no precipitation | Clear liquid state, no precipitation |
| | 35° C. | | | Clear liquid state, no precipitation | Clear liquid state, no precipitation | Clear liquid state, no precipitation | Clear liquid state, no precipitation |
| | 40° C. | | | Clear liquid state, no precipitation | Clear liquid state, no precipitation | Clear liquid state, no precipitation | Clear liquid state, no precipitation |
| | 60° C. | | | Clear liquid state, no precipitation | Clear liquid state, no precipitation | Clear liquid state, no precipitation | Clear liquid state, no precipitation |
| Freezing recoverability | | | | Clear liquid state, no precipitation | Clear liquid state, no precipitation | Clear liquid state, no precipitation | Clear liquid state, no precipitation |

| | | | | Example 4 | | Comparative example 2 | |
|---|---|---|---|---|---|---|---|
| | | | | 4-10 | 4-11 | 2-1 | 2-2 |
| Sulfosuccinate ester composition | Composition (mass %) | (A) | Sodium sulfosuccinate ester (1)*[1] | 40 | 35 | 75 | 76 |
| | | (B) | Propylene glycol | 30 | 32.5 | 20 | 4 |
| | | (C) | Sodium sulfate | 0.17 | 0.15 | 0.3 | 0.3 |
| | | (D) | Ion exchange water | 29.0 | 31.6 | 3.5 | 18.5 |
| | | (Y) | Maleic acid diester*[1] | 0.8 | 0.7 | 1.2 | 1.2 |
| | | | Total amount | 100 | 100 | 100 | 100 |
| A/(A + B + C + D) (mass ratio) | | | | 0.40 | 0.35 | 0.76 | 0.77 |
| B/(A + B + C + D) (mass ratio) | | | | 0.30 | 0.33 | 0.20 | 0.04 |
| C/(A + B + C + D) (mass ratio) | | | | 0.0017 | 0.0015 | 0.0030 | 0.0030 |
| D/(A + B + C + D) (mass ratio) | | | | 0.29 | 0.32 | 0.04 | 0.19 |

TABLE 4-continued

| | | | | | |
|---|---|---|---|---|---|
| D/(A + D) (mass ratio) | | 0.42 | 0.47 | 0.04 | 0.20 |
| (A + B)/(A + B + C + D) (mass ratio) | | 0.71 | 0.68 | 0.96 | 0.81 |
| Uniformity | 25° C. | Clear liquid state, no precipitation | Clear liquid state, no precipitation | Turbidity, precipitation | No fluidity |
| | 35° C. | Clear liquid state, no precipitation | Clear liquid state, no precipitation | Turbidity, precipitation | No fluidity |
| | 40° C. | Clear liquid state, no precipitation | Clear liquid state, no precipitation | Turbidity, precipitation | No fluidity |
| | 60° C. | Clear liquid state, no precipitation | Clear liquid state, no precipitation | Turbidity, precipitation | No fluidity |
| Freezing recoverability | | Clear liquid state, no precipitation | Clear liquid state, no precipitation | Turbidity, precipitation | No fluidity |

*[1]The reaction product of production example 1 was used.

TABLE 5

| | | | | Example 5 | |
|---|---|---|---|---|---|
| | | | | 5-1 | 5-2 |
| Sulfosuccinate ester composition | Composition (mass %) | (A) | Sodium sulfosuccinate ester (2)*[2] | 65 | 65 |
| | | (B) | Propylene glycol | 15 | 15 |
| | | (C) | Sodium sulfate | 0.3 | 0.5 |
| | | | Sodium sulfite | 0.05 | 0.3 |
| | | (D) | Ion exchange water | 17.95 | 17.1 |
| | | (Y) | Maleic acid diester*[2] | 1.7 | 2.1 |
| Total amount | | | | 100 | 100 |
| A/(A + B + C + D) (mass ratio) | | | | 0.66 | 0.66 |
| B/(A + B + C + D) (mass ratio) | | | | 0.15 | 0.15 |
| C/(A + B + C + D) (mass ratio) | | | | 0.004 | 0.008 |
| D/(A + B + C + D) (mass ratio) | | | | 0.18 | 0.17 |
| D/(A + D) (mass ratio) | | | | 0.22 | 0.21 |
| (A + B)/(A + B + C + D) (mass ratio) | | | | 0.46 | 0.47 |
| Uniformity | | | 25° C. | Clear liquid state, no precipitation | Clear liquid state, no precipitation |
| | | | 35° C. | Clear liquid state, no precipitation | Clear liquid state, no precipitation |
| | | | 40° C. | Clear liquid state, no precipitation | Clear liquid state, no precipitation |
| | | | 60° C. | Clear liquid state, no precipitation | Clear liquid state, no precipitation |
| Freezing recoverability | | | | Clear liquid state, no precipitation | Clear liquid state, no precipitation |

*[2]The reaction product of production example 2 was used.

The invention claimed is:

1. A sulfonate composition, comprising:

a compound represented by the following formula (1) as component (A):

$$ROOC—(CH_2)_p—CH(SO_3M)—CH_2—(CH_2)_q—COOR' \quad (1)$$

wherein M represents an alkali metal ion, R and R' represent 2-propylheptyl group, p and q each represent a number of 0 or more and 18 or less, and a total of p and q is 0 or more and 18 or less;

an organic solvent as component (B);

at least one inorganic metal compound selected from the group consisting of an alkali metal sulfate, an alkali metal carbonate, an alkali metal hydrogen carbonate, an alkali metal hydroxide, and an alkaline earth metal hydroxide as component (C); and water as component (D), wherein A/(A+B+C+D), which is a mass ratio of the component (A) to a total content of the components (A), (B), (C) and (D), is 0.05 or more and 0.71 or less, B/(A+B+C+D), which is a mass ratio of the component (B) to the total content of the components (A), (B), (C) and (D), is 0.05 or more, C/(A+B+C+D), which is a mass ratio of the component (C) to the total content of the components (A), (B), (C) and (D), is more than 0, and D/(A+B+C+D), which is a mass ratio of the component (D) to the total content of the components (A), (B), (C) and (D) is more than 0.10 and less than 0.60.

2. The sulfonate composition according to claim 1, wherein the component (B) is at least one selected from the group consisting of a monohydric alcohol and a polyhydric alcohol.

3. The sulfonate composition according to claim 1, wherein the component (B) is a monohydric alcohol, and the composition satisfies the following condition (Ia) or the following condition (Ib):

condition (Ia):

A/(A+B+C+D) is 0.05 or more and 0.71 or less,
B/(A+B+C+D) is more than 0.05,
C/(A+B+C+D) is more than 0 and less than 0.001, and
D/(A+B+C+D) is more than 0.10 and 0.50 or less;

condition (Ib):

A/(A+B+C+D) is 0.05 or more and 0.71 or less,
B/(A+B+C+D) is 0.05 or more,
C/(A+B+C+D) is 0.001 or more, and
D/(A+B+C+D) is 0.15 or more and less than 0.60.

4. The sulfonate composition according to claim 3, wherein the composition satisfies the condition (Ia), which further includes a condition that a mass ratio of a total content of the components (A) and (B) to the total content of the components (A), (B), (C) and (D) is more than 0.10 and less than 0.90.

5. The sulfonate composition according to claim 3, wherein the composition satisfies the condition (Ib), which further includes a condition that a mass ratio of a total content of the components (A) and (B) to the total content of the components (A), (B), (C) and (D) is 0.10 or more and 0.80 or less.

6. The sulfonate composition according to claim 1, wherein the component (B) is a polyhydric alcohol, and the composition satisfies the following condition (IIa) or the following condition (IIb):

condition (IIa):

A/(A+B+C+D) is 0.05 or more and 0.71 or less,
B/(A+B+C+D) is more than 0.05 and 0.90 or less,
C/(A+B+C+D) is more than 0 and less than 0.001, and
D/(A+B+C+D) is more than 0.10 and less than 0.50;

condition (IIb):

A/(A+B+C+D) is 0.05 or more and 0.71 or less,
B/(A+B+C+D) is more than 0.05 and less than 0.40,
C/(A+B+C+D) is 0.001 or more, and
D/(A+B+C+D) is 0.13 or more and less than 0.50.

7. The sulfonate composition according to claim 6, wherein the composition satisfies the condition (IIa), which further includes a condition that a mass ratio of a total content of the components (A) and (B) to the total content of the components (A), (B), (C) and (D) is 0.40 or more and 0.95 or less.

8. The sulfonate composition according to claim 6, wherein the composition satisfies the condition (IIb), which further includes a condition that a mass ratio of a total content of the components (A) and (B) to the total content of the components (A), (B), (C) and (D) is 0.40 or more and 0.95 or less.

9. The sulfonate composition according to claim 1, wherein A/(A+B+C+D) is 0.3 or more.

10. The sulfonate composition according to claim 1, wherein A/(A+B+C+D) is 0.4 or more.

11. The sulfonate composition according to claim 1, wherein A/(A+B+C+D) is 0.5 or more.

12. The sulfonate composition according to claim 1, wherein C/(A+B+C+D) is less than 0.018.

13. The sulfonate composition according to claim 1, wherein C/(A+B+C+D) is less than 0.016.

14. The sulfonate composition according to claim 1, wherein D/(A+B+C+D) is 0.13 or more.

15. The sulfonate composition according to claim 1, wherein a mass ratio of the component (C) to the component (A), C/A, is 0.020 or less.

16. The sulfonate composition according to claim 1, wherein the component (B) is a compound selected from the group consisting of methanol, ethanol, 1-propanol, 1-butanol, 1-pentanol, 1-hexanol, 1-heptanol, 1-octanol, 1-nonanol, 2-nonanol, 5-nonanol, 1-decanol, 1-dodecanol, 3,5,5-trimethylhexan-1-ol, 2,6-dimethyl-4-heptanol, 2-propylheptanol, 4-methyl 2-propylhexanol, and 5-methyl 2-propylhexanol.

17. The sulfonate composition according to claim 1, wherein the component (B) is a compound selected from the group consisting of ethylene glycol, propylene glycol, 1,3-butanediol, 1,4-butanediol, 1,5-pentanediol, 1,6-hexanediol, 1,10-decanediol, diethylene glycol, triethylene glycol, tetraethylene glycol, dipropylene glycol, tripropylene glycol, glycerin, xylitol, and sorbitol.

18. The sulfonate composition according to claim 1, wherein the component (B) is a compound selected from the group consisting of ethanol, 1-butanol, 1-propanol, glycerin, and propylene glycol.

19. The sulfonate composition according to claim 1, wherein the total content of the components (A), (B), (C) and (D) in the sulfonate composition is 90 mass % or more and 100 mass % or less.

* * * * *